United States Patent [19] [11] 3,932,666
Bennett [45] Jan. 13, 1976

[54] TREATMENT OF TREES FOR PREVENTION AND CURE OF WILT DISEASES

[75] Inventor: David J. Bennett, Manlius, N.Y.

[73] Assignee: Environmental Technology Corporation, Bloomington, Minn.

[22] Filed: Apr. 15, 1974

[21] Appl. No.: 460,764

Related U.S. Application Data

[63] Continuation-in-part of Ser. No. 323,056, Jan. 12, 1973, abandoned.

[52] U.S. Cl. ............................... 424/341; 424/347
[51] Int. Cl.² ........................................ A01N 9/24
[58] Field of Search ..................... 424/340, 341, 347

[56] References Cited
OTHER PUBLICATIONS

Yearbook of Agriculture–Insects (1952), pp. 677–680.
Chemical Abstracts, Vol. 58, (1963), p. 2798a.
Chemical Abstracts, Vol. 65, (1966), p. 2930a.
Chemical Abstracts, Vol. 61, (1964), p. 13221e.

*Primary Examiner*—V. D. Turner
*Attorney, Agent, or Firm*—Schroeder Siegfried Ryan & Vidas

[57] ABSTRACT

A treatment for trees infected with fungus diseases producing characteristic wilt which comprises injecting a solution including as the active ingredient thereof a halogenated compound structurally similar to the lignin. Typical examples include halogenated compounds of the creosols, catechol and dimethoxy toluene.

10 Claims, No Drawings

TREATMENT OF TREES FOR PREVENTION AND CURE OF WILT DISEASES

The present application is a Continuation-in-Part of my copending patent application Ser. No. 323,056 filed Jan. 12, 1973 now abandoned, entitled PROPHYLACTIC TREATMENT OF TREES FOR WILT DISEASES and assigned to the same assignee as the present invention.

It is well known that a number of tree diseases are brought about by fungus infection of the vascular system. Two noted examples of such infections are oak wilt and Dutch elm disease, respectively caused by the fungi "ceratocystis fagacearum" and "ceratocystis ulmi." The latter disease is most widely known for the destruction of American elms (*Ulmus Americana*), a preferred street and shade tree common to the east and midwest portions of the United States.

In each of these diseases, the fungus can be spread by means of root grafts, although the most common vector is bark beetles. The introduction of the European bark beetle (*scolytis multistriatus*) has been a major factor resulting in the rapid spread of Dutch elm disease. The present invention is directed to a treatment of trees which is prophylactic in its effect, as preventing the onset of the disease as well as having curative effects on trees which are already affected. By curative is meant that the spread of the disease is at least arrested so that by removal of diseased branches the remainder of the tree will remain healthy.

Treatment of vascular diseases in the past has taken the form of foliar sprays, soil drenches and systemic injections. Of the above, systemic injection is the most desirable method of insuring intimate contact of the fungicide with the disease-causing fungus. While prior investigators have proposed a number of treatments purporting to act as a cure for the control of such fungus diseases, none of them have proved satisfactory to the extent of gaining widespread and successful usage. In order for a fungicide to be satisfactory for the intended purpose, it must possess a high fungitoxicity and low phytotoxicity. That is to say, the fungicide must inhibit further fungus growth without causing any extensive damage to the host tree.

In accordance with the present invention, it has been discovered that by selecting compounds which are structurally similar to the lignins of the trees as the treating agent the compounds are compatible chemically with the tree and tend to produce little, if any, adverse effect upon the tree itself. By halogenating these compounds—preferably with chlorine—the compounds are made highly toxic to the fungus which brings about either oak wilt or Dutch elm disease.

The chemical structure of the lignins has been extensively investigated by many individuals over a period of years. While the structure of the lignin is not known with complete certainty, it is known to be of a polymeric construction and is quite probably a polymer of the basic building block indicated below.

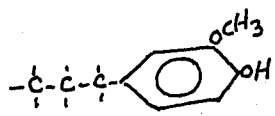

See *Construction and Biosynthesis of Lignin* by K. Freudenberg et al., Springer-Verlag New York Inc.

In accordance with the invention, it has been found that if compounds having a structure similar to that given above are halogenated and then introduced into the vascular system of the tree by the injection technique that at least temporary protection of a tree against infection by either Dutch elm or oak wilt disease, respectively, can be achieved. For those trees which are already infected, treatment with the chemical compounds in accordance with the present invention arrests further progress of the diseases.

The majority of the compounds in accordance with the invention are only sparingly soluble in water. Therefore, it is necessary to prepare a solution of the active treatment chemical in a suitable carrier that will achieve its distribution through the circulatory system of the tree. While a number of solvents are suitable for the purpose, it has been found that either methyl or ethyl alcohol and aqueous mixtures thereof are particularly useful for dissolving the compounds to be used in the treatment.

The following examples will more specifically illustrate the nature of the treatment in accordance with the present invention.

EXAMPLE I

The first class of compounds which will be illustrated are the halogenated creosols. This class of compounds is the preferred form of the invention. It has been found that creosols having a structural formula as indicated below may be suitably treated to halogenate the same at either or both of the five and six positions on the ring.

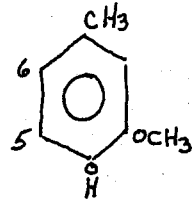

3-methoxy-4-hydroxytoluene

A single halogenation with chlorine to produce either 5 or 6 chloro creosol produces a compound having sufficient toxicity to the fungus which brings about either Dutch elm or oak wilt diseases. The treatment material is effectively distributed throughout the tree by the trees own vascular system.

When aqueous solutions of either 5 or 6-chlorocreosol were introduced to cultures (potato-dextrose agar) of ceratocystis ulmi, inhibitory growth effects were noted at concentration levels of 10 milligrams per liter of the chloro creosol in a suitable carrier. At a concentration level of 100 milligrams per liter, fungus growth was no longer maintained in the culture.

In treatment of a tree a solution of a creosol in methyl alcohol was made by mixing 100 milliliters of 6 chloro creosol in one gallon of methyl alcohol. The quantity injected into a tree to achieve the desired results will, of course, depend upon the size of the tree. For a 24-inch diameter trunk and a 40-foot high tree, it has been found that one gallon of solution is a desirable amount. Larger concentration and/or larger total amount of active ingredient may be used, but as the above concentration and total amount provides the desired prophylactic or disease arrest treatment no useful purposes are served by use of more material.

Lesser concentration levels of the active ingredient and smaller total quantity for the same size tree may be used. However, the indicated amount is believed optimum. The concentration will, obviously, be above the 10 milligrams per liter concentration (and preferably above 100 milligrams per liter) noted previously at which inhibitory effects on the growth of the fungus are found.

For smaller or larger trees one may proportion to the size of the tree and by simple arithmetic make adjustment as to the amount to be injected.

Sampling of trees treated in accordance with the above procedure, which trees had previously been tested to establish the existence of Dutch elm disease, resulted in all cases in arrest of further spread of the disease following treatment.

The trees so treated showed no short-term adverse effects to the foliage from the treatment and in the subsequent year to treatment were free of further incursions by the Dutch elm disease. In some instances there was an apparent increase in the number of sucker branches and leaves in the growing season subsequent to treatment.

Treatment with 5 chloro creosol and 5,6-dichloro creosol in similar concentrations and quantities per equivalent tree size produce substantially the same beneficial results. Of course, one may also use mixtures of each of the three enumerated chlorinated creosols.

It is of interest to note that the compound 5-chloro-creosol is relatively rapidly destroyed upon exposure to ordinary environments exterior to the vascular system of the tree. This is of importance as it shows that adverse environmental impact from accidental introduction into the soil or water is at most minimal in time. That is, it is not a persistent compound with long-term contaminant possibility.

EXAMPLE II

A second class of compounds useful in treatment of infected trees in accordance with the invention is the Catechol series that has been halogenated to produce the desired toxicity of the compound to the fungus inducing the wilt diseases. THe structural formula for the preferred compound of the Catechol series, 6 chloro Catechol, is given below:

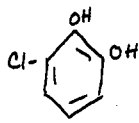

As in the case for the compounds illustrated in Example I above, a quantity of this compound is dissolved in a suitable carrier, which is typically methyl or ethyl alcohol, in the same proportions as in Example I and is injected into the xylem layer of the elm tree. Distribution of the compound occurs through the vascular system of the elm tree and is effective in preventing the initial infection by the fungus or alternatively, if the fungus has already infected the tree, to prevent its further spread.

Various substitutions can be made in this basic Catechol structure to produce closely related compounds capable of achieving the prophylactic effects of the invention. For example, a compound such as 5-methyl Catechol may be suitably modified by introduction of chlorine at either or both of the 3 and 4 positions and used in like proportions as the active ingredient for injection into a tree. Likewise, homologues of the Catechol such as veratrole which has been halogenated to produce the desired toxicity are similarly effective in treatment of trees infected with Dutch elm or to prevent infection by the Dutch elm fungus. Other related compounds include chlorinated coniferyl alcohol, vanillin and the like.

EXAMPLE III

A substituted veratrole, 5-chloro-3,4 dimethoxytoluene, was prepared and mixed in a methyl alcohol carrier in the quantity corresponding to that of Example I. Elm trees were injected with the resulting solution in concentration and quantity corresponding to those given for Example I with the results obtained being substantially the same as those for the creosols and Catechols of the previous examples.

The technique for injection of the active chemicals and carrier may follow the prior art practices of injecting solutions into trees for similar purposes. In the interest of introducing the treatment chemical and carrier at a rapid rate, I prefer to introduce a quarter-inch diameter tube through the bark into the cambium layer and then inject by means of this quarter-inch tube the solution into the tree under approximately 100 pounds per square inch pressure. As a fluid is compatible with the existing structures and fluids of the tree, it is rapidly disseminated throughout the tree by this technique. The time involved is of very short order which provides an important economic advantage for the treatment of numerous trees per unit time by an operator. For greater speed in injection, a plurality of such injection tubes may be used. For simplification of the injecting apparatus, a simple gravity feed may also be used.

What is claimed is:

1. A method for the treatment of elm trees for the fungus disease of the vascular system thereof caused by ceratocystis ulmi which comprises injecting into the vascular system of the tree an alcoholic carrier solution of a fungicidally effective quantity of a chlorinated compound selected from the group consisting of 5-chloro-creosol, 6-chloro-creosol, 5,6,-dichloro-creosol, 6-chloro-catechol, 5-chloro-3,4-dimethoxy-toluene, 3-chloro-5 methyl-catechol, and 4-chloro-5 methyl-catechol.

2. The method in accordance with claim 1 wherein the chlorinated compound is selected from the group consisting of 5-chloro-creosol, and 6-chloro-creosol, 5,6-dichloro-creosol, 6-chloro-catechol and 5-chloro-3,4-dimethoxy-toluene.

3. The method in accordance with claim 2 wherein the active treating agent is a chlorinated creosol selected from the group consisting of 5-chloro-creosol and 6-chloro creosol dissolved in ethyl alcohol as a carrier.

4. The method in accordance with claim 2 wherein the active treating agent is selected from the group consisting of 5-chloro-creosol and 6-chloro-creosol dissolved in methyl alcohol as a carrier.

5. The method in accordance with claim 2 wherein the active agent is 5-chloro-creosol.

6. The method in accordance with claim 4 wherein the concentration of the active treating agent is greater than 10 milligrams per liter in the carrier.

7. The method in accordance with claim 2 wherein the active agent is 6-chloro-catechol dissolved in methyl alcohol as a carrier.

8. The method in accordance with claim 1 wherein the active agent is a 5-chloro-3,4-dimethoxy-toluene.

9. The method in accordance with claim 2 wherein the active treating agent is 5-chloro-creosol in a concentration of about 100 milliliters per gallon in methyl alcohol.

10. The method in accordance with claim 4 wherein the active agent is 6-chloro-creosol.

* * * * *